United States Patent [19]

Desjarlais

[11] Patent Number: 4,642,383
[45] Date of Patent: Feb. 10, 1987

[54] FAST COUPLING LEMON-YELLOW PHENOLIC COUPLERS

[75] Inventor: Robert C. Desjarlais, South Hadley, Mass.

[73] Assignee: James River Graphics, Inc., South Hadley, Mass.

[21] Appl. No.: 428,457

[22] Filed: Sep. 30, 1982

[51] Int. Cl.$^4$ ............................................ C07C 148/00
[52] U.S. Cl. .......................................... 568/48; 568/29; 568/33; 568/34; 568/37; 8/524; 430/60
[58] Field of Search ........................ 568/29, 33, 34, 48, 568/37

[56] References Cited

U.S. PATENT DOCUMENTS

| | | | |
|---|---|---|---|
| 1,989,065 | 1/1935 | Schmidt et al. | 95/7 |
| 2,353,735 | 7/1944 | Kunz et al. | 568/48 |
| 2,531,004 | 11/1950 | Slifkin | 95/6 |
| 2,537,001 | 1/1951 | von Glahn et al. | 95/6 |
| 2,537,106 | 1/1951 | von Glahn et al. | 95/6 |
| 2,542,560 | 2/1951 | Neumann | 95/6 |
| 2,542,566 | 2/1951 | Fedlow | 95/6 |
| 2,560,049 | 7/1951 | Cook | 568/37 |
| 2,717,832 | 9/1955 | Sulich, Jr. | 95/6 |
| 2,814,597 | 11/1957 | Wenneis et al. | 568/48 |
| 3,092,585 | 6/1963 | Orloff | 568/48 |
| 3,099,639 | 7/1963 | Cobb et al. | 568/48 |
| 3,471,576 | 10/1969 | Klesper et al. | 568/33 |
| 3,573,052 | 3/1971 | Gray et al. | 96/91 |
| 3,591,381 | 7/1971 | Gray et al. | 96/75 |
| 3,619,191 | 11/1971 | Desjarlais | 96/75 |
| 3,785,826 | 1/1974 | Slimowicz et al. | 96/75 |
| 3,857,896 | 12/1974 | Desjarlais | 568/37 |
| 3,881,931 | 5/1975 | Tsubota et al. | 96/49 |
| 3,917,715 | 11/1975 | Leslie et al. | 568/33 |
| 4,089,904 | 5/1978 | Cisney et al. | 568/37 |
| 4,275,240 | 6/1981 | Yamaguchi et al. | 568/37 |

FOREIGN PATENT DOCUMENTS

| | | | |
|---|---|---|---|
| 0622112 | 6/1961 | Canada | 568/33 |
| 1493941 | 9/1966 | France | 568/29 |

OTHER PUBLICATIONS

Chem. Abstracts 92: 111705c (1980).

*Primary Examiner*—George F. Lesmes
*Assistant Examiner*—S. A. Gibson
*Attorney, Agent, or Firm*—Burns, Doane, Swecker & Mathis

[57] ABSTRACT

Substituted 2,2'-dihydroxydiphenyl sulfide, sulfoxide, and sulfone compounds, and their use as azo coupling components in light-sensitive diazo compositions. The novel compounds couple with rapidly developing diazonium compounds to provide lemon-yellow dyes, and can be used in combination with blue and violet couplers to provide a green-black diazo image in higher density areas with a neutral black in lower density areas.

2 Claims, No Drawings

FAST COUPLING LEMON-YELLOW PHENOLIC COUPLERS

BACKGROUND OF THE INVENTION

1. Field of the Invention

The present invention relates to diazo photoreproduction, and more particularly, to coupling compounds for use in diazo photoreproduction.

2. Description of the Prior Art

In semi-dry or two component diazotype photoreproduction, one or more coupling components are included as ingredients of a sensitizing composition. The sensitizing composition also includes a diazo sensitizer which decomposes when subjected to actinic radiation. Accordingly, after exposure, coupling between the coupling component or components and the diazo sensitizer can only occur in those areas where decomposition was not complete. Development is effected by subjecting the exposed composition to alkaline atmosphere, e.g., by bringing it into contact with ammonia vapors, to neutralize the acidic inhibitor with the concomitant formation of dyestuff in the non-exposed areas due to coupling of the residual diazo compound and the coupling components.

Although the color of the azo dye image which is obtained in any given instance depends primarily on the coupling components and the diazonium compounds which are employed, coupling components are typically described as being couplers of a given color, with the color being the color of the dye which is usually obtained when the particular coupler in question couples with a diazonium compound. For example, couplers such as monohydric phenols, catechols, catechol derivatives, resorcinols, resorcinol derivatives, diketones, acetoacetic acid derivatives, acetonitriles, cyanoacetamides and the like, usually result in yellow, orange, sepia, brown, red or maroon azo dyes. Thus, couplers from such classes of materials are conveniently referred to as yellow, orange, sepia, brown, red, or maroon couplers. On the other hand, couplers such as hydroxy naphthoic acid derivatives, dioxynaphthalene derivatives, pyronones, hydroxypyridones, and the like, usually result in blue or violet azo dyes, and thus are conveniently referred to as blue or violet couplers.

One group of highly useful coupling components are the yellow couplers, since the dyes obtained from these couplers usually have actinic absorption characteristics which permit their use as the sole coupler in a diazo composition which is employed to prepare diazotype "masters" or intermediates, and since couplers from this group can often be employed as shading components when used in conjunction with another coupler or couplers. As indicated above, compounds containing active methylene groups, compounds such as acetonitriles, derivatives of acetonitriles, and the like, have been employed as yellow couplers in diazo compositions, (cf., for example, U.S. Pat. Nos. 1,989,065; 2,531,004, 2,537,001; and 2,537,106), yet a number of these active methylene types of couplers have exhibited a tendency, when employed in two-component diazo compositions, to precouple with the diazonium compound which is present in said compositions during storage even in the presence of the stabilizers which are usually employed. This tendency to precouple prior to exposure and development has limited the use of these materials somewhat, since even a slight amount of precoupling can result in the formation of an azo dye in those areas of the diazotype material which are the background or "cleared" areas of the diazotype print. In addition to this tendency to precouple, a number of these prior-art, active-methylene types of couplers also result, upon coupling, in dyes which have an undesirable reddish hue and/or which have a tendency to fade upon subsequent exposure to light.

It should be apparent from the above, that, in addition to obtaining a single-color azo dye image, one should be able to obtain a mixture of azo dyes (and thus a mixture of colors) by including more than one coupling component or more than one diazonium compound in the light-sensitive diazo composition. Thus, by a proper choice of coupling components and/or diazonium compounds, one should be able to obtain a wide variety of colors in the resulting azo dyes, including black. However, the achievement of a uniform color over a wide range of image densities from a diazo composition containing more than one coupling component has proven difficult to obtain in actual practice. In order to obtain a uniform color over a wide range of image densities, it is essential to carefully match the coupling activity of the various coupling components with the diazonium compound or compounds which are employed, and that the combined absorptions of the azo dyes produced from the various couplers cover the entire visible spectrum. It is also essential that none of the azo dyes produced from the various coupling components be subject to a "color-shift" or change of shade due to a change in pH, for example, after ammonia has evaporated from the film. Otherwise, the resulting dye image of the diazotype material may shift from the neutral point.

Thus although resorcinol sulfides, resorcinol sulfoxides (for example, see U.S. Pat. No. 2,717,832 and 3,785,826) and diresorcinols (for example, see U.S. Pat. No. 2,542,560 and 2,542,566) are several classes of yellow azo coupling components which exhibit excellent resistance to subsequent fading to light, these particular classes of yellow coupling components unfortunately exhibit a severe tendency to color-shift when incorporated into black-line formulations. Similarly, AON's such as 1-hydroxy-2-naphthoic acid piperidide also exhibit a severe tendency to color-shift when incorporated into black-line formulations. In addition, these compounds are ultraviolet absorbers and readily discolor with light.

Attempts have also been made to employ alkyl substituted resorcinols (e.g., 2-alkyl resorcinols) and dialkyl substituted resorcinols (e.g., 2,4-dialkyl resorcinols) in blackline formulations. Although the diazotype materials resulting from such formulations exhibit little or no tendency to color-shift, these particular classes of resorcinol coupling components have a relatively slow rate of coupling and are readily oxidized to colored oxidation products.

Phenolic couplers such as o-biphenol, 1,2-bis-o-hydroxy phenyl cyclopropane, meta-cresyl glutaric acid, and the hydroxyethyl ether of catechol are commercially used to give lemon-yellow colors. However, their coupling activity leaves much to be desired. Although neutral blacks are obtained in the high density areas, the blue (violet-coupling) coupler predominates in the lower density areas and a two-toned print is obtained.

There have also been attempts to produce modified diresorcinols for use as coupling components. For example, U.S. Pat. Nos. 3,573,052 and 3,591,381 state that the following class of hindered phenols as stabilizers for use with blue and yellow couplers:

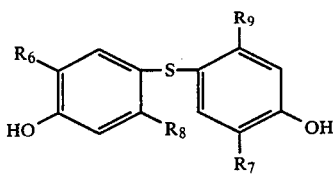

wherein each of $R_6$ to $R_9$ is an alkyl radical, and $R_6$ and $R_7$ are preferably tertiary alkyl radicals. The '052 patent further discloses the following compounds:

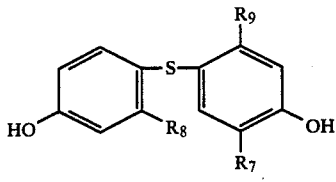

wherein $R_7$-$R_9$ are alkyl radicals having between one and eighteen carbon atoms.

U.S. Pat. Nos. 3,619,191 and 3,857,896 disclose the synthesis and use of the following diresorcyl sulfide and sulfoxide compounds as orange or sepia couplers in a diazo process:

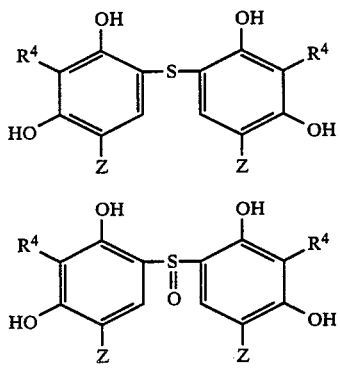

wherein $R^4$ is hydrogen, an alkyl group containing from one to six carbon atoms, an unsubstituted aryl group or halo-substituted aryl group, an aralkyl group, an alkaryl group, an alkoxy group having from one to six carbon atoms, an aryloxy group, an aralkoxy group, or a halogen; and Z is a hydrogen or halogen atom.

U.S. Pat. No. 3,881,931 discloses a yellow coupler of the following general formula:

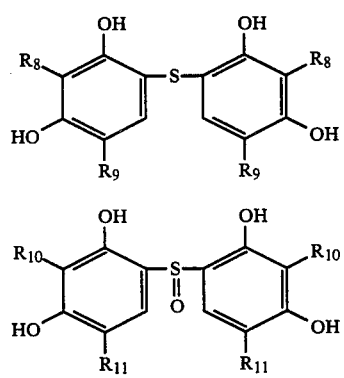

wherein $R_8$ ad $R_{10}$ each represent an alkyl group having one to four carbon atoms, and $R_9$ and $R_{11}$ each represents either a hydrogen atom or a halogen atom.

However, in spite of the activity in this area, a need continues to exist for coupling components which give lemon-yellow colors with rapid developing diazonium compounds, are resistant to light oxidation, are resistant to oxidation to colored products, are not UV absorbers, couple very rapidly, and do not exhibit pH ammonia shift of the dyes once formed.

SUMMARY OF THE INVENTION

The present invention provides compounds of the following general formula:

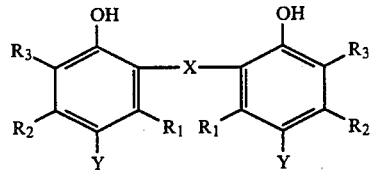

wherein:
$R_1$, $R_2$, and $R_3$ are the same or different and are selected from the group consisting of hydrogen, a halogen atom, alkyl of about 1 to 6 carbon atoms, aralkyl, aryl of about 6 to 10 carbon atoms, branched alkyl of about 1 to 6 carbon atoms, alkoxy of about 1 to 6 carbon atoms, and alkylthio, at least one of $R_1$, $R_2$, and $R_3$ being other than hydrogen or a halogen atom;
X is S, SO, or $SO_2$; and
Y is hydrogen or a halogen atom.

These novel coupling components provide lemon-yellow colors, are resistant to light oxidation, are not UV absorbers, couple very rapidly, and do not exhibit pH ammonia shift of the dyes after formation.

DETAILED DESCRIPTION OF THE INVENTION

As stated above, the lemon-yellow coupling components of the present invention are compounds of the general formula:

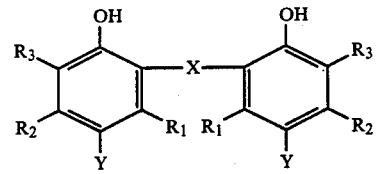

wherein $R_1$, $R_2$, and $R_3$ are the same or different and are selected from the group consisting of hydrogen, a halogen atom, alkyl of about 1 to 6 carbon atoms, aralkyl, aryl of about 6 to 10 carbon atoms, branched alkyl of about 1 to 6 carbon atoms, alkoxy of about 1 to 6 carbon atoms, and alkylthio, at least one of $R_1$, R2 and $R_3$ being other than hydrogen or a halogen atom; X is S, SO, or $SO_2$; and Y is hydrogen or a halogen atom.

Preferred compounds within this group are those in which $R_1$ and $R_3$ are selected from methyl, ethyl, isopropyl or a halogen atom and $R_2$ is hydrogen; and wherein $R_1$ and either $R_2$ and $R_3$ are hydrogen with the other of either $R_2$ or $R_3$ being selected from other than hydrogen or a halogen atom. Particularly preferred are 2,2'-dihydroxy-3,3',6,6'-tetramethyl diphenyl sulfide (i.e. $R_2$ and Y are hydrogen; $R_1$ and $R_3$ are methyl; X is S); 2,2'-dihydroxy-3,3'-dimethyldiphenyl sulfide (i.e., $R_1$, $R_2$ and Y are H; and $R_3$ is methyl); and 2,2'-dihydroxy-3,3'-diisopropyl-6,6'-dimethyldiphenyl sulfide (i.e., $R_1$ is methyl; $R_2$ is hydrogen; and $R_3$ is isopropyl).

Such compounds can be prepared by reacting an appropriately substituted phenol with sulfur dichloride in the presence of an inert solvent. Temperatures of from about 5° C. to about 35° C. are preferred, with temperatures of from about 5° to about 15° C. being particularly preferred with the lower-boiling inert solvents. The reaction may, if desired, be conducted under an atmosphere of a stream of dry, inert gas to facilitate the removal of the hydrogen chloride which is evolved. The resulting compounds are easily recovered as crystalline solids having relatively high melting points. The sulfoxide and sulfone derivatives of these sulfides are prepared by treating the sulfide with an appropriate amount of an oxidizing agent, such as hydrogen peroxide, chromic oxide, potassium permanganate, and the like.

Synthesis of the compounds of the present invention is facilitated by the use of starting phenols which are substituted by halogen in the position para to the hydroxy group. The predominant reaction of a phenol with sulfur dichloride is para substitution. Thus, 4-halogen substituted phenols are used to block the 4 position. This leaves the 2-position open for substitution. After this has been completed, if desired, the 4 position can be unblocked by reductive dehalogenation.

The light sensitive diazonium compounds which can be employed in preparing the light-sensitive diazo compositions of the present invention are any of the numerous light-sensitive diazonium compounds which are available in the prior art, and the particular light-sensitive diazonium compound which is employed is not critical in the practice of this invention. Illustrative of such compounds are the stabilized salts or double salt complexes of diazonium derivatives of a p-phenylenediamine, for example, stabilized salts of diazonium derivatives of such compounds as N-methyl-p-phenylenediamine, N-ethyl-p-phenylenediamine, N-hydroxyethyl-p-phenylenediamine, N-methyl-N-(beta-hydroxyethyl)-p-phenylenediamine, N-ethyl-N-(beta-hydroxyethyl)-p-phenylenediamine, N-butyl-N-(beta-hydroxyethyl)-p-phenylenediamine, N,N-di-(beta-hydroxyethyl)-p-phenylenediamine, N-benzyl-N-ethyl-p-phenylenediamine, N-ethyl-2-methyl-4-aminoaniline, N,N-dimethyl-2-methyl-4-aminoaniline, N,N-dimethyl-3-methyl-4-aminoaniline, N,N-diethyl-3-methyl-4-aminoaniline, N-ethyl-N-(beta-hydroxyethyl)-3-methyl-4-aminoaniline, N-cyclohexyl-2-methoxy-4-aminoaniline, N,N-di(beta-hydroxyethyl)-3-methyl4-aminoaniline, 2,5-diethoxy-4-morpholinoaniline, 2,5-dimethoxy-4-morpholinoaniline, 2,5-dibutoxy-4-morpholinoaniline, 2,5-diisopropoxy-4-morpholinoaniline, 2,5-diethoxy-4-piperidinoaniline, 2,5-dimethoxy-4-piperidinoaniline, 2,5-diisopropoxy-4-(N'-benzoyl)piperidinoaniline, N-benzyl-2,5-diethoxy-4-aminoaniline, 2,6-dimethyl-4-morpholinoaniline, 2,6-diethyl-4-morpholinoaniline, 2,6-dimethyl-4-piperidinoaniline, N,N-diethyl-2-chloro-4-aminoaniline, N,N-dimethyl-2-chloro-4-aminoaniline, N,N-dibutyl-2-chloro-4-aminoaniline, 4-pyrrolidino-3-methylaniline, 4-pyrrolidino-3-chloroaniline, 4-amino-2,5-diethoxy-4'-methyldiphenyl sulfide, 4-amino-2,5-dimethoxy-4'-methyldiphenyl sulfide, 4-amino-2,5-diethoxy-4'-methoxydiphenyl, 4-dimethylamino-2-chloro-5-(4'-chloro)-phenoxyaniline, 4-diethylamino-2-chloro-5-(4'-chloro)-phenoxyaniline and the like.

The nature of the salt used to stabilize or complex the diazonium derivative is not critical, and can be, for example, a zinc chloride double salt, a cadmium chloride double salt, a tin chloride double salt, a borofluoride salt, a sulfate salt, a hexafluorophosphate salt, and the like.

A particularly preferred class of diazonium compounds for use herein is that set forth in copending Application Ser. No. 428,455, filed concurrently herewith, and incorporated herein by reference. The compounds disclosed therein are represented by the following formula:

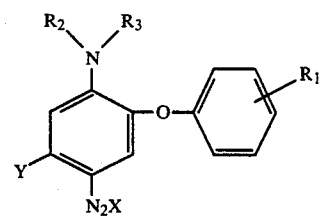

wherein
$R_1$ is tertiary butyl or tertiary amyl, preferably in a position para to the oxygen of the phenoxy group;
Y is hydrogen, alkyl, hydroxyalkyl, cyanoalkyl, cycloalkyl, aralkyl, alkoxy, aryloxy, aralkoxy, aralkylthio, arylthio, alkylthio, halogen, allyl, allyloxy, allylthio, cyanoalkoxy, hydroxyalkoxy, methoxyalkoxy, trifluoroalkyl, alkylacetylamino, morpholino, dialkyl carbonamido, and the like;
$R_2$ and $R_3$ are the same or different and are alkyl, aralkyl, allyl, cyanoalkyl, hydroxyalkyl, hydrogen, acyl, cycloalkyl, beta-chloroalkyl, branched alkyl, or a structure wherein $R_2$ and $R_3$ may be linked together to form a heterocyclic structure, optionally including a sulfur atom, an oxygen atom, or a substituted trivalent nitrogen atom, e.g. morpholino, piperidino, thiomorpholino, piperazino, pyrrolidino; and
X is an anion.

Particularly preferred within this class of preferred compounds are those in which $R_1$ is t-butyl, $R_2$ and $R_3$ are both methyl or ethyl or combine to form a morpholino group, and Y is hydrogen, a halogen, methyl, ethyl, methoxy, morpholino, a thioether, a phenoxy group, or a substituted phenoxy group.

It should be understood that mixtures of light-sensitive diazonium compounds can be employed in the practice of the present invention without departing from the scope thereof, and that other couplers can be employed in conjunction with the yellow couplers hereinbefore described in preparing diazo compositions in accordance with the present invention without departing from the scope thereof. In this regard, of particular interest are black-line diazo compositions comprising one or more couplers from the particular class of lemon-yellow azo coupling components set forth above in full detail, along with one or more light-sensitive diazonium compounds and one or more BON blue azo coupling components such as 2-hydroxy-3-naphthoic acid, 2'-methoxyanilide; 2-hydroxy-3-naphthoic acid, 2'5'-dimethylanilide; 6-methoxy-2-hydroxy-3-naphthoic acid-2'-methyl anilide, 2-hydroxy-3-naphthoic acid-3'-trifluoromethyl anilide, 2-hydroxy-3-naphthoic acid-2'-methyl anilide, 2-hydroxy-3-naphthoic acid-2'-ethyl anilide, 2-hydroxy-3-naphthoic acid-2'-methoxy anilide and the like. A listing of preferred blue couplers is also provided in U.S. Pat. No. 3,619,191, incorporated herein by reference. Such black-line formulations provide black-line diazotype materials which are light-stable (i.e. are fade resistant), are storage-stable (i.e. are resistant to precoupling), and are resistant to colorshift with changes in pH.

The light-sensitive diazo compositions of this invention can also comprise any of the additional components which are often employed in such compositions, such as stabilizers, preservatives, antioxidants, extenders, inhibitors, color intensifiers, and the like.

The various components of the light-sensitive diazo compositions of this invention are usually dissolved in an organic solvent system, and the resulting solution is then coated, using conventional coating techniques, onto a suitable base support. The base supports which can be employed are any of those commonly used as support materials in the photographic and copying arts, such as paper, cloth, films and the like. Illustrative of the films which can be employed are films such as cellulose ether films, cellulose ester films (e.g., cellulose acetate and cellulose acetate butyrate), polyester films (e.g., polyethylene terephthalate), and the like. Upon drying, the base support which has been coated with a light-sensitive diazo composition of this invention results in a light-sensitive diazotype material which can then be imaged and developed in the manner which is conventional and well-known in the diazotype art. Such diazotype materials find use in the fields of engineering drawing reproduction, microfilm duplication, visual communications and the graphic arts.

In order to further illustrate the present invention and the advantages thereof, the following specific examples are given, it being understood that they are intended only to be illustrative without limiting the scope of the present invention.

EXAMPLE I

Representative Synthesis of a Lemon-Yellow Coupler of the Present Invention

A. Preparation of 4-bromo-o-cresol

Into a 5-liter reaction flask was charged 324g of o-cresol (3 moles) and 1200 g of methylene chloride. The reaction was cooled to 2° C. and 480 g (3 moles) of bromine dissolved in 960 g of methylene chloride was run in slowly over a 7-hour period. The next day, the cooling bath was removed and a heating mantle was attached. 1 liter of Isopar G (trademark of Exxon for a hydrocarbon fraction) was added and distillation of the methylene chloride was begun under water aspirator vacuum. Eventually the distillation rate slowed and the pot temperature rose to 70° C. The still head temperature dropped from 35° C. to 28° C. The solution was poured into a beaker and cooled to room temperature without stirring. In the morning, the solution was cooled to −5° C. and filtered. There was recovered 440 g of 4-bromo-o-cresol melting at 61–64° C. in 78% yield.

B. Preparation of 2,2'-dihydroxy-3,3'-dimethyl-5,5'-dibromodiphenyl sulfide

Into a 3 liter reaction flask was charged in 440 g (2.35 moles) of 4-bromo-o-cresol and 700 ml of methylene chloride. The temperature dropped to 18° C. Then 121g (1.18 moles) of freshly distilled sulfur dichloride was added fairly rapidly. HCL was evolved. The temperature was maintained at 14° C. by external cooling. Hydrogen chloride gas continued to evolve with a precipitate forming during the addition of sulfur dichloride. The solution was stirred for 2 hours with cooling to 4° C. after which 700 ml of hexane was added. After stirring the precipitate was filtered and washed with hexane, and then air dried overnight. There was recovered 248g of product melting at 162–164° C. in 52% yield.

C. Preparation of 2,2'-dihydroxy-3,3-dimethyl-diphenyl sulfide reductive dehalogenation)

Into a 3 liter reaction flask was charged 128 g (32 moles) of NaOH. Next was added with stirring 1141 ml of water. When all of the sodium hydroxide was dissolved, a pinch of zinc dust was added. Next, 258 g (0.64 moles) of the brominated sulfide was added, which dissolved with stirring. Then 207 g of zinc dust (3.2 moles) was added and the mixture was refluxed overnight with stirring. The mixture was filtered hot after which the zinc cake was extracted with 100 ml of 10% NaOH (hot). The clear colorless liquors were combined, cooled, acidified with 200 ml of 36% hydrochloric acid, and then heated to liquify the product. The solution was then cooled and the solid nuggets which formed were filtered out. The nuggets were then suspended in water, heated to liquify them while keeping the solution acidic by the addition of hydrochloric acid as necessary. After cooling, the solid lumps were filtered. These were dissolved in hot Isopar G (trademark of Exxon for a hydrocarbon fraction) and the excess water distilled out. The product dissolved in hot Isopar G (trademark of Exxon for a hydrocarbon fraction) was decanted from a small amount of black tars clinging to the vessel. The decanted solution was cooled to room temperature and then to −5° C. The resulting crystals were filtered, washed with hexane and air dried, to recover 154 g of product melting at 72°–78° C. (98% yield).

In a similar manner were prepared:

2,2'-dihydroxy-3,3',6,6'-tetramethyl diphenyl sulfide M.P. 125°–128° C.

2,2'-dihydroxy-3,3'-diisopropyl-6,6'-dimethyl diphenyl sulfide M.P. 115°–120° C.

2,2'-dihydroxy-3,3',4,4',6,6'-hexamethyl diphenyl sulfide M.P. 125°–135° C.

2,2'-dihydroxy-5,5'-dibromo-3,3',6,6'-tetramethyl diphenyl sulfide M.P. 171°–173° C.

2,2'-dihydroxy-5,5'-dichloro-3,3',6,6'-tetramethyl diphenyl sulfide M.P. 176°–178° C.

2,2'-dihydroxy-5,5'-dibromo-3,3',4,4',6,6'-hexamethyl diphenyl sulfide M.P. 195°–205° C.

EXAMPLE II

A solution of the following was prepared:

| Ingredients | Amount (grams) |
| --- | --- |
| Methanol | 78 |
| Acetone | 57 |
| Methyl ethyl ketone | 15 |
| 2-hydroxy-3-naphthoic acid-3' acetylanilide | 1.1 |
| 5-sulfosalicylic acid | 2.3 |
| 6-methoxy-2-hydroxy-3-naphthoic acid-2'-methyl anilide | .3 |
| 2-chloro-4-N,N—dimethyl amino-5-(4'-tert.-butyl)-phenoxy benzene diazonium tetrafluoborate | 3.0 |

The mix was divided into 6 equal portions and to each was added yellow couplers of Table 1 in the amounts shown in Table 1.

The solutions were bead imbibition coated onto polyester films (containing a suitable bonding layer and an overcoat of cellulose acetate propionate of approximately 0.25 mils thickness). The films were dried for 5 minutes at 70° C. The films were processed in the ordinary manner (i.e., using a Kodak #2 photographic step tablet as a master, the films were exposed in a Scott 716 TM microprinter equipped with a Gallium doped mercury vapor lamp followed by development in a Tecnifax TM Model 6000 ammonia developer which had an ammonia feed rate of 1.3 ml./min. of 26° Baume ammonia introduced onto a hot plate whereby ammonia gas and water vapor are delivered to the film surface).

The results obtained are shown in Table 1. Compound IV is a yellow coupler of the present invention. Compounds I–III and VI are representative compounds of the prior art for comparison purposes. Compound V is a known compound but has not previously been suggested as a coupler.

TABLE 1

| | Amount (grams) | Name | Dye Color (D. Max Area) | Dye Color (Lower Density Area) |
|---|---|---|---|---|
| I | .18 | Catechol, mono hydroxyethyl ether | Plum-black | Violet |
| II | .27 | 1,2-bis-ortho hydroxy phenyl cyclopropane | Black | Violet |
| III | .29 | Meta Cresol Glutaric acid | Violet | Violet |
| IV | .30 | 2,2'dihydroxy-3,3'dimethyl-diphenyl sulfide | Green-Black | Plum-Black |
| V | .26 | 2,2'dihydroxy-diphenyl sulfide | Greenish black | Violet-Black |
| VI | .36 | catechol, mono hydroxyethyl ether | Black | Violet |

Based on the above results, the coupling speeds of these compounds are rated as follows:

IV>V>II>I>III

Note that Compound VI and Compound I are the same compound with the amount simply doubled. Comparing IV to VI results in a rating of IV>VI.

Since the object is to obtain as neutral a black image as possible with as little yellow coupler as possible, it is readily seen that the compound of the present invention is superior to the prior art. Very slow coupling compounds require large amounts of material in the mix and yet exhibit bitonal effects.

EXAMPLE III

A solution of the following was prepared:

| Ingredients | Amount (grams) |
|---|---|
| Methanol | 52 |
| Acetone | 38 |
| Methyl ethyl ketone | 10 |
| 5-sulfosalicylic acid | 1.52 |
| 2-hydroxy-3-naphthoic acid-3'-acetylanilide | .74 |
| 6-methoxy-2-hydroxy-3-naphthoic acid-2'-methyl anilide | .20 |
| 2-chloro-4-N,N—dimethylamino-5-(4'-tert.-butyl)phenoxy benzene | 2.00 |
| diazonium tetrafluoborate | |

The solution was divided into two equal portions and to each was added the yellow couplers listed in Table 2 in the amounts shown in Table 2. The solutions were coated, dried and processed as in Example II.

TABLE 2

| | Amount (grams) | Name | Dye Color (D. Max Area) | Color (Lower Density Area) |
|---|---|---|---|---|
| IV | .60 | 2,2'-dihydroxy-3,3'-dimethyl-diphenyl sulfide | Green-Black | Plum-Black |
| VII | .66 | 2,2'-dihydroxy-3,3',6,6'-tetra-methyl-diphenyl sulfide | Yellow-Black | Green-Black |

It is immediately evident that Compound VII couples much faster than Compound IV. In fact, reduction of the amount of Compound VII in the same formulation to 0.28 to 0.30 gms resulted in a continuous neutral black over a wide range of densities indicating that Compound VII couples twice as fast as Compound IV. If instead of Compound VII, there is used 2,2'-dihydroxy-3-3'-diisopropyl-6,6'-dimethyldiphenyl sulfide in an equimolar amount, similar results would be obtained, although the color would be a slight plum-black with a yellow dye which is not as stable to UV light as the preferred compounds. If 2,2'-dihydroxy-5,5'-dibromo-3,3',6,6'tetramethyl diphenyl sulfide is used, similar results are obtained.

EXAMPLE IV

Solutions of the following were prepared:

| Component | Amount (grams) | Function |
|---|---|---|
| Acetone | 18.79 | Solvent |
| Methanol | 18.79 | " |
| Methyl cellosolve | 4.18 | " |
| Eastman CAP-482-20 Cellulose Acetate Propionate | 5.01 | Polymer |
| 5-Sulfosalicylic acid | .57 | Acid |
| Thiourea | .12 | Antioxidant |
| Tryptophan | .05 | " |
| Riechold Stabilite Antioxidant 49-470 | .28 | " |
| 2-hydroxy-3-naphthoic acid-2'-ethyl anilide | .50 | Blue coupler |
| 2,2'-dihydroxy-3,3',6,6' tetramethyl diphenyl sulfide | .36 | Yellow coupler |
| 2,2',4,4'-tetrahydroxydiphenyl sulfide | .03 | Sepia coupler |
| 4-Morpholino-2,5-diisopropoxy benzene diazonium tetrafluoborate | 1.01 | Diazo |
| Tributyl citrate | .10 | Development Accelerator |

The solution measured 1000 centipoise viscosity and was coated onto a 7 mil polyester film containing a suitable bonding layer using a #30 wire wound Mayer rod. The fim was dried for 3 minutes at 85° C. in a convection oven. Next the film was cut into rectangular pieces (105×148 mm) and processed in an Addressograph/Multigraph OP-50$^R$ Bruning diazo microfiche duplicator at exposure setting 7. To illustrate the independence of temperature on the color of the diazo microfiche, these films were developed at 140° F., 160° F., and 180° F. respectively. The results are as follows:

| Temp (°F.) | Initial Color | Prints Aired of Ammonia |
| --- | --- | --- |
| 140 | Green-Black | Green-Black |
| 160 | Green-Black | Green-Black |
| 180 | Green-Black | Green-Black |

The results indicate the excellent developing latitude of this coupling component. If, instead of the 2,2'-dihydroxy-3,3',6,6'-tetramethyl diphenyl sulfide, there is used 2,2',4,4'-tetrahydroxy-3,3'-dimethyl diphenyl sulfide (or sulfoxide) a severe colorshift of the yellow dye is observed from deep plum-black when first developed, to a slightly plum-black when aired of ammonia.

Similarly, use of the morpholine amide of 1-hydroxy-2 naphthoic acid would result in the same general results as with the above tetrahydroxy compounds.

In addition, both of the tetrahydroxy compounds described above would not result in a film of the same color at 140° F. 160° F. or 180° F. but instead would be blue-black at 180° F. and reddish brown at 140° F. developing temperature.

While the invention has been described in terms of various preferred embodiments, one skilled in the art will appreciate that various modifications, substitutions, omissions, and changes may be made without departing from the spirit thereof. Accordingly, it is intended that the scope of the present invention be limited solely by the scope of the following claims.

What is claimed is:
1. 2,2'-dihydroxy-3,3',6,6'-tetramethyl diphenyl sulfide.
2. 2,2'-dihydroxy-3,3'-diisopropyl-6,6'-dimethyl diphenyl sulfide.

* * * * *